(12) United States Patent
Belgrader et al.

(10) Patent No.: US 7,955,841 B2
(45) Date of Patent: Jun. 7, 2011

(54) TEMPERATURE CONTROL DEVICE WITH A FLEXIBLE TEMPERATURE CONTROL SURFACE

(75) Inventors: Phil Belgrader, Severna Park, MD (US); Christopher G. Cooney, Severn, MD (US); Robert Doebler, Upland, CA (US); Anna Hickerson, Altadena, CA (US); Bruce Irvine, Glendora, CA (US); Ali Nadim, San Marino, CA (US); James Sterling, Upland, CA (US); Reza Miraghaie, Culver City, CA (US)

(73) Assignee: Akonni Biosystems, Frederick, MD (US)

( * ) Notice: Subject to any disclaimer, the term of this patent is extended or adjusted under 35 U.S.C. 154(b) by 217 days.

(21) Appl. No.: 12/232,669

(22) Filed: Sep. 22, 2008

(65) Prior Publication Data
US 2009/0087903 A1   Apr. 2, 2009

Related U.S. Application Data

(63) Continuation-in-part of application No. 11/843,843, filed on Aug. 23, 2007.

(51) Int. Cl.
*C12M 1/38* (2006.01)

(52) U.S. Cl. ........... 435/303.1; 435/91.2; 422/138

(58) Field of Classification Search .......... 435/6, 303.1, 435/91.2; 422/131, 138; 165/104.11, 80.5, 165/111, 158, 165
See application file for complete search history.

(56) References Cited

U.S. PATENT DOCUMENTS

| | | | |
|---|---|---|---|
| 5,851,492 A * | 12/1998 | Blattner | 422/102 |
| 6,086,679 A | 7/2000 | Lee | |
| 6,345,610 B1 | 2/2002 | Yang | |
| 2002/0143437 A1* | 10/2002 | Handique et al. | 700/266 |
| 2004/0209331 A1* | 10/2004 | Ririe | 435/91.2 |
| 2006/0246580 A1 | 11/2006 | Kim et al. | |
| 2009/0053772 A1* | 2/2009 | Belgrader | 435/91.2 |

FOREIGN PATENT DOCUMENTS
JP      03111108      5/1991

\* cited by examiner

*Primary Examiner* — William H Beisner
*Assistant Examiner* — Michael Hobbs
(74) *Attorney, Agent, or Firm* — Andrews Kurth LLP

(57) ABSTRACT

A device for controlling temperature in a reaction chamber is disclosed. The device comprises: a bladder assembly comprising a housing dimensioned to hold a reaction chamber disposed within an interior volume of the housing; and a first temperature-control bladder disposed within the housing, the first temperature-control bladder is configured to receive a temperature-control fluid and comprises a flexible, heat conductive surface that comes in contact with at least a portion of an exterior surface of the reaction chamber after receiving the temperature-control fluid. Also disclosed are a bladder thermal cycler, a temperature-control bladder assembly and methods for producing a thermal cycle in a reaction chamber.

11 Claims, 17 Drawing Sheets

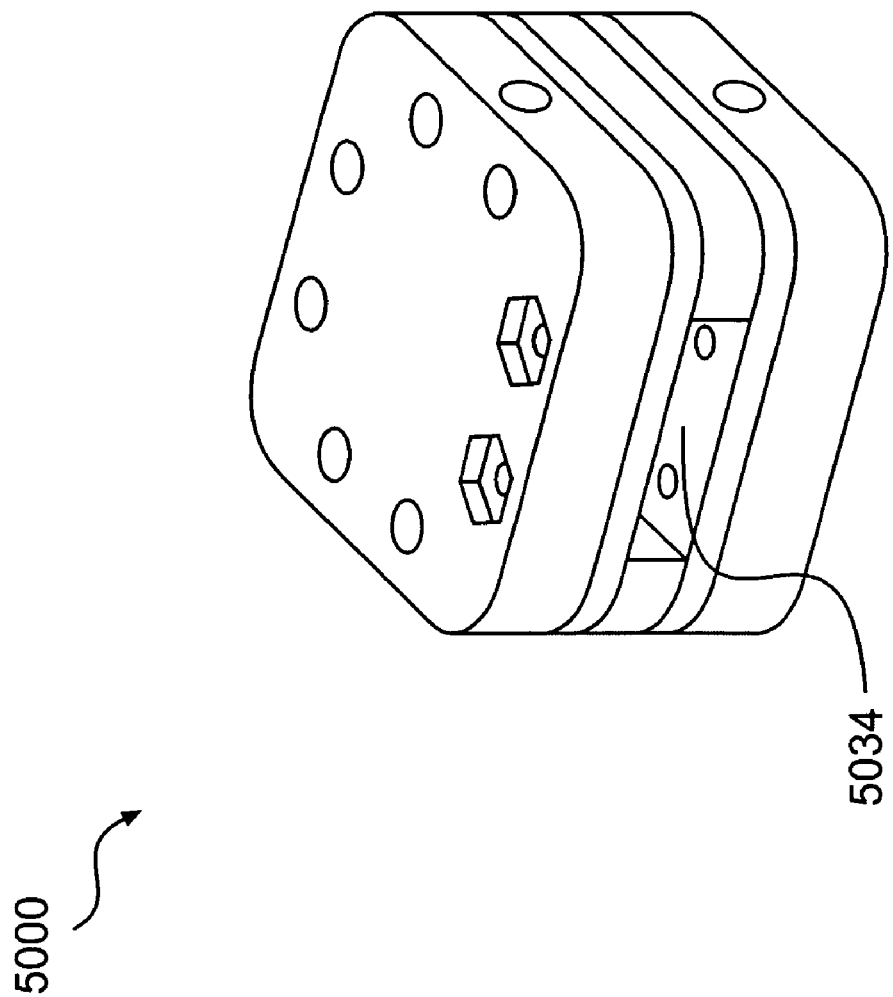

TEMPERATURE CONTROL DEVICE WITH A FLEXIBLE TEMPERATURE CONTROL SURFACE

CROSS-REFERENCE TO RELATED APPLICATION(S)

This application is a continuation-in-part of U.S. patent application Ser. No. 11/843,843 filed Aug. 23, 2007, entitled "THERMAL CYCLER FOR PCR INCLUDING TEMPERATURE CONTROL BLADDER," the subject matter of which is herein incorporated by reference in its entirety.

TECHNICAL FIELD

The technical field is temperature control devices and, in particular, temperature control devices with a flexible temperature control surface.

BACKGROUND

Many chemical and biochemical analysis methods require rapid and precise change of reaction temperature during the analysis. For example, polymerase chain reaction (PCR) has been widely used in biochemical laboratories. A fundamental operation during the PCR process is thermal cycling, i.e., the raising and lowering of reaction temperatures to enable the amplication of target DNA sequences. A PCR thermal cycle typically has four segments: heating the sample to a first temperature; maintaining the sample at the first temperature; cooling the sample to a lower temperature; and maintaining the temperature at the lower temperature. Conventional PCR instrumentation typically uses an aluminum block holding as many as ninety-six conical reaction tubes in which the sample and necessary reagents for amplication are contained. The block is heated and cooled during the PCR amplication process, often using either a Peltier heating/cooling apparatus, or a closed-loop liquid heating/cooling system in which flowing through channels machined into the aluminum block. However, the large mass of the aluminum block, and the thermal conductivity of aluminum, limit the rates of heating and cooling to about 1° C. per second; so a fifty-cycle PCR amplification process takes at least about two hours.

Moreover, the cooling rate of the aluminum block is significantly lower than the heating rate. The asymmetry between the heating and cooling rates reduces the efficiency of the PCR process. For example, unwanted side reactions can occur at temperatures between the extremes creating unwanted DNA products, such as so-called "primer-dimers" and anomalous amplicons that consume reagents necessary for the desired PCR reaction. Other processes, e.g., ligand binding (organic or enzymatic) also suffer from unwanted side reactions under non-uniform temperatures that often degrade the analysis. For these reasons, optimization of the PCR process and similar biochemical reaction processes requires that the desired optimal reaction temperatures be reached as quickly as possible, spending minimal time at intermediate temperatures. Therefore, the reaction vessels containing the reactants must be designed to optimize heating and cooling rates, to permit real time optical interrogation, and to accept various sample volumes.

Rigid heaters are not ideal for heating other rigid surfaces like microarrays. Especially when PCR and microarray hybridization are performed in a single chamber. Microarrays are typically spotted on glass or plastic slides that need to be rigid for proper immobilization of the oligonucleotides on the surface and for subsequent detection of captured, extended, or generated product. Thus, there remains a need for a better approach to interface a heater with a rigid reaction chamber.

SUMMARY

A device for controlling temperature in a reaction chamber is disclosed. The device includes a bladder assembly including a housing that defines an interior volume and is dimensioned to hold a reaction chamber disposed within an interior volume of the housing, and a first temperature-control bladder disposed within the housing. The first temperature-control bladder is configured to receive a temperature-control fluid and includes a flexible, heat conductive surface that comes in contact with at least a portion of an exterior surface of the reaction chamber after receiving the temperature-control fluid.

Also disclosed is a bladder thermal cycler that includes a bladder assembly configured to receive a reaction chamber. The bladder assembly includes a housing defining an interior space accessible through an opening and at least one temperature-control bladder having a thermal conductive surface. The temperature-control bladder is inflatable with a temperature-control fluid and the thermal conductive surface forms a contact with an exterior surface of a reaction chamber placed within the interior space when the temperature-control bladder is inflated. The bladder assembly also includes a first temperature control device capable of bringing said temperature-control fluid to a first temperature when the temperature-control fluid passes through the first temperature control device, a second temperature control device capable of bringing said temperature-control fluid to a second temperature when the temperature-control fluid passes through the second temperature control device, a first fluid control device that delivers the temperature-control fluid to the bladder assembly at the first temperature, a second fluid control device that delivers the temperature-control fluid to the bladder assembly at the second temperature; and a system controller that controls the temperature control devices and fluid control devices.

Also disclosed is a temperature-control bladder assembly. The temperature-control bladder assembly includes a top bracket comprising a first temperature-control bladder, a bottom bracket including a second temperature-control bladder, and a middle bracket that, when assembled with the top bracket and bottom bracket, defines an interior space. The first and second bladders form contacts with a reaction chamber placed inside the interior space when inflated with a temperature-control fluid.

Also disclosed is a method for producing a thermal cycle in a reaction chamber having thermal contact with a temperature-control bladder. The method includes (a) filling the temperature-control bladder with a temperature-control fluid at a first temperature; (b) filling the temperature-control bladder with the temperature-control fluid at a second temperature; and (c) repeating steps (a) and (b).

Also disclosed is a method for producing a thermal cycle in a reaction chamber. The method includes: placing a reaction chamber in the vicinity of a temperature-control bladder having a thermal conductive surface, the thermal conductive surface forms a contact with an exterior surface of the reaction chamber when said temperature-control bladder is filled with a temperature control fluid, filling the temperature-control bladder with the temperature-control fluid at a first temperature, withholding the temperature-control fluid at the first temperature in the temperature-control bladder for a first period of time, filling the temperature-control bladder with the temperature-control fluid at a second temperature, and withholding the temperature-control fluid at the second temperature in the temperature-control bladder for a second period of time.

BRIEF DESCRIPTION OF DRAWINGS

The detailed description will refer to the following drawings, wherein like numerals refer to like elements, and wherein:

FIG. 1A is a partial cut-away view of such a device. FIG. 1B is a cut-away top view of the interior of such a device, with the bladder in a substantially deflated state. FIG. 1C is a cut-away top view of the interior of such a device, with the bladder in a substantially inflated state to provide thermal contact with a reaction vessel.

FIGS. 5A-5D are schematics showing an embodiment of a modular bladder assembly. FIG. 5A shows individual components of the modular bladder assembly. FIG. 5B shows an assembled modular bladder assembly. FIG. 5C shows a pillow-shaped bladder. FIG. 5D shows a bladder assembly with two inflated pillow bladders.

DETAILED DESCRIPTION

Figure 1A:
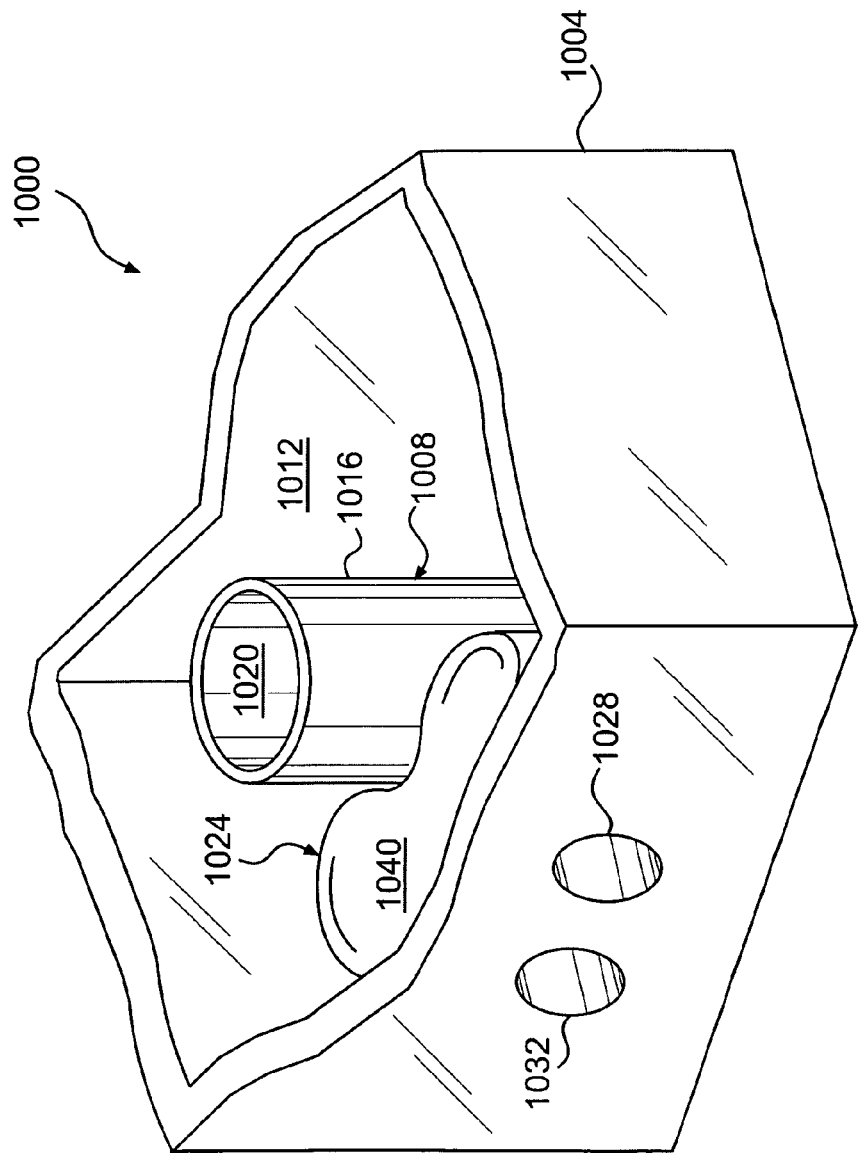
FIGS. 1A, 1B, and 1C illustrate one embodiment of a device in accordance with the present invention.

This description is intended to be read in connection with the accompanying drawings, which are to be considered part of the entire written description of this invention. The drawings are not necessarily to scale and certain features of the invention may be shown exaggerated in scale or in somewhat schematic form in the interest of clarity and conciseness. In the description, relative terms such as "front," "back," "up," "down," "top" and "bottom," as well as derivatives thereof, should be construed to refer to the orientation as then described or as shown in the drawing under discussion. These relative terms are for convenience of description and normally are not intended to require a particular orientation. Terms concerning attachments, coupling and the like, such as "connected" and "attached," refer to a relationship wherein structures are secured or attached to one another either directly or indirectly through intervening structures, as well as both movable or rigid attachments or relationships, unless expressly described otherwise.

The term "temperature-control bladder," as used in the embodiments described herein, refers to a hollow, flexible container with a thermal conductive surface. A temperature-control bladder can be of any shape and size. When filled or inflated with a temperature-control fluid, the temperature-control bladder is capable of facilitating heat transfer between the temperature-control fluid inside the temperature-control bladder and an object that is in contact with the thermal conductive surface of the temperature-control bladder.

The term "fluid," as used in the embodiments described herein, refers to a substance that continually deforms (flows) under an applied shear stress regardless of how small the applied stress. Fluids are a subset of the phases of matter and include liquids, gases, aerosols (particles in a gas stream), gels, plasmas and, to some extent, solids.

In describing embodiments of the present invention, specific terminology is employed for the sake of clarity. However, the invention is not intended to be limited to the specific terminology so selected. It is to be understood that each specific element includes all technical equivalents which operate in a similar manner to accomplish a similar purpose.

In a first aspect, the present invention provides a device for controlling the temperature of a defined volume. In one embodiment, the defined volume is a reaction chamber configured for holding chemical reactants and performing a chemical reaction therein at controlled temperatures. In one embodiment, shown in FIG. 1A, a temperature control device 1000 includes a housing 1004 defining an interior space 1012. The housing 1004 can be constructed from materials and designs well known to persons having ordinary skill in the art. Examples of such materials include, without limitation, plastics, metals, ceramics, composites, and the like. Examples of housing embodiments include those in which the housing is of lightweight construction (e.g., thin plastic), hermetically sealed (e.g., for containing harmful substances, such as hazardous chemical and biological substances), or capable of holding a vacuum in the interior space. Thus, in some embodiments, the housing 1004 includes means for reducing the pressure (i.e., inducing a vacuum) within the within interior space 1012 of the housing 1004. In other embodiments, the housing 1004 includes one or more inlets or ports for adding reagents. The housing 1004 may also include sensors, reactant supplies, and other components as will be familiar to those persons having ordinary skill in the art. Still more designs and specifications will be familiar to persons having ordinary skill in the art. The particular choices of materials and design will depend on the anticipated function and operating conditions of the device as will be understood by persons having ordinary skill in the art.

Referring again to FIG. 1A, the temperature control device 1000 further comprises a reaction chamber 1008 arranged within the interior space 1012 of the housing 1004. The reaction chamber 1008 includes a thermally conductive chamber wall 1016 that defines an internal volume 1020 within the reaction chamber 1008. The reaction chamber 1008 can be constructed from materials and designs well known to persons having ordinary skill in the art. Examples of such materials include, without limitation, plastics, metals, ceramics, composites, and the like. Exemplary embodiments include those in which the reaction chamber is of lightweight construction (e.g., thin plastic), hermetically sealed (e.g., for containing harmful substances, such as hazardous chemical and biological substances), or capable of holding a vacuum.

In some embodiments, the reaction chamber 1008 is designed to hold a single mixture of materials and, in more particular embodiments, includes a cap or other seal to create a closed chamber. Still more designs and specifications will be familiar to persons having ordinary skill in the art. For example, the reaction chamber may include one or more inlets or ports for adding reagents or removing reaction products, internal sensors, and windows for external sensors. The particular choices of materials and design will depend on the anticipated function and operating conditions of the device as will be understood by persons having ordinary skill in the art.

Referring again to FIG. 1A, also disposed within the interior 1012 of the housing 1004 are one or more temperature-control bladders 1024 that are disposed proximal to the reaction chamber 1008 and configured to control, mediate, or otherwise modify the temperature of the internal volume 1020 of the reaction chamber 1008. The temperature-control bladder 1024 is composed of a material having suitable mechanical and thermal properties, as will be understood by persons having ordinary skill in the art. Examples of suitable materials include, but are not limited to, silicone, foil, latex, mylar, polyurethane, polypropylene, and polyethlene. Each temperature-control bladder 1024 is configured to accept a temperature-control fluid, such as a liquid or gas, that is introduced into an interior space 1040 of the temperature-control bladder 1024 through an inlet 1028 and removed from an outlet 1032. In one embodiment, the temperature-control fluid is stored in a reservoir or other repository in which the temperature-control fluid is maintained at a desired temperature. In another embodiment, the reservoir does not have any temperature controlling function. The temperature of the temperature-control fluid is manipulated by a temperature controller located between the reservoir and the temperature-control bladder 1024. The temperature controller is a heater or a heater/cooler combination that is capable of rapidly change the temperature of the temperature-control fluid as the fluid passes through the temperature controller.

Figure 1B:
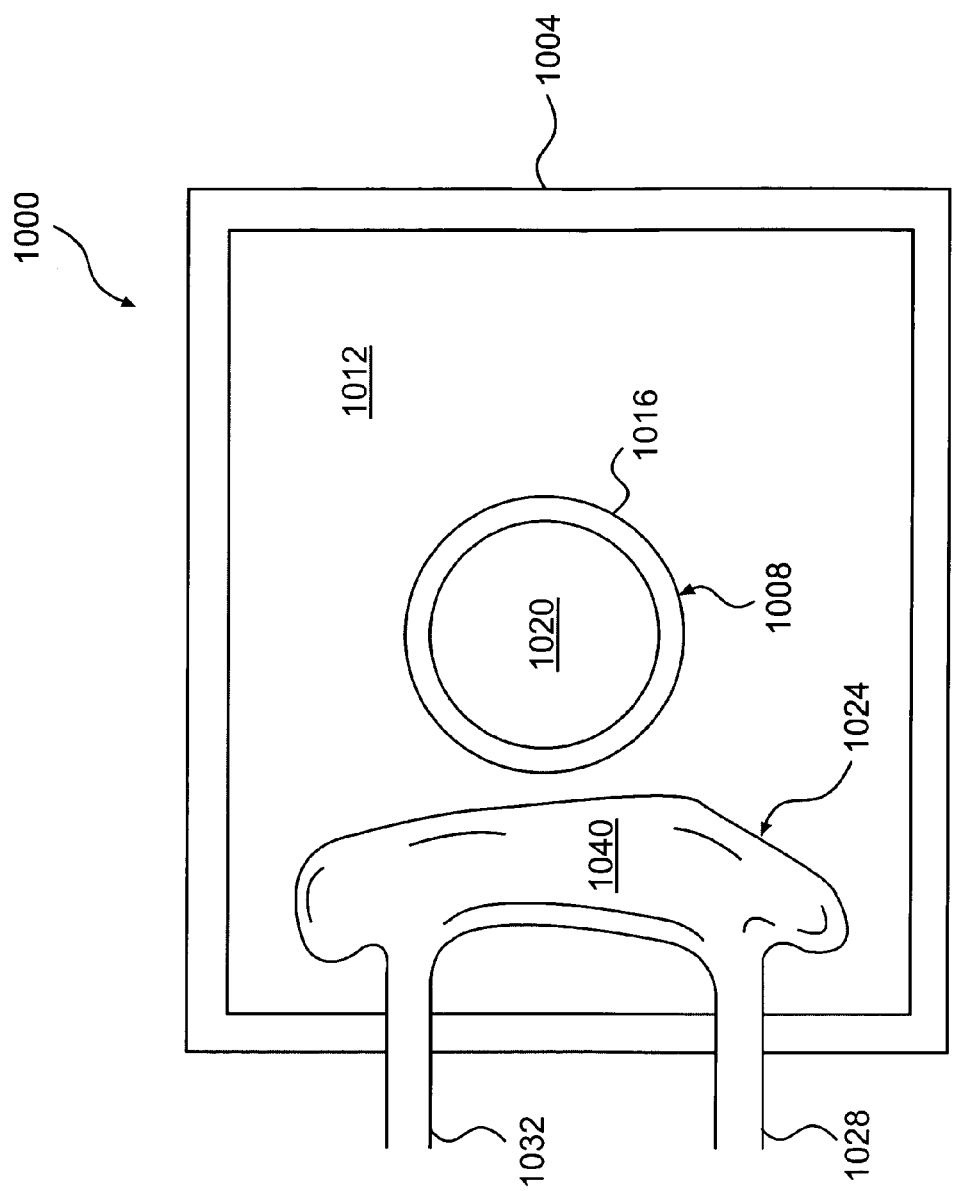
Figure 1C:
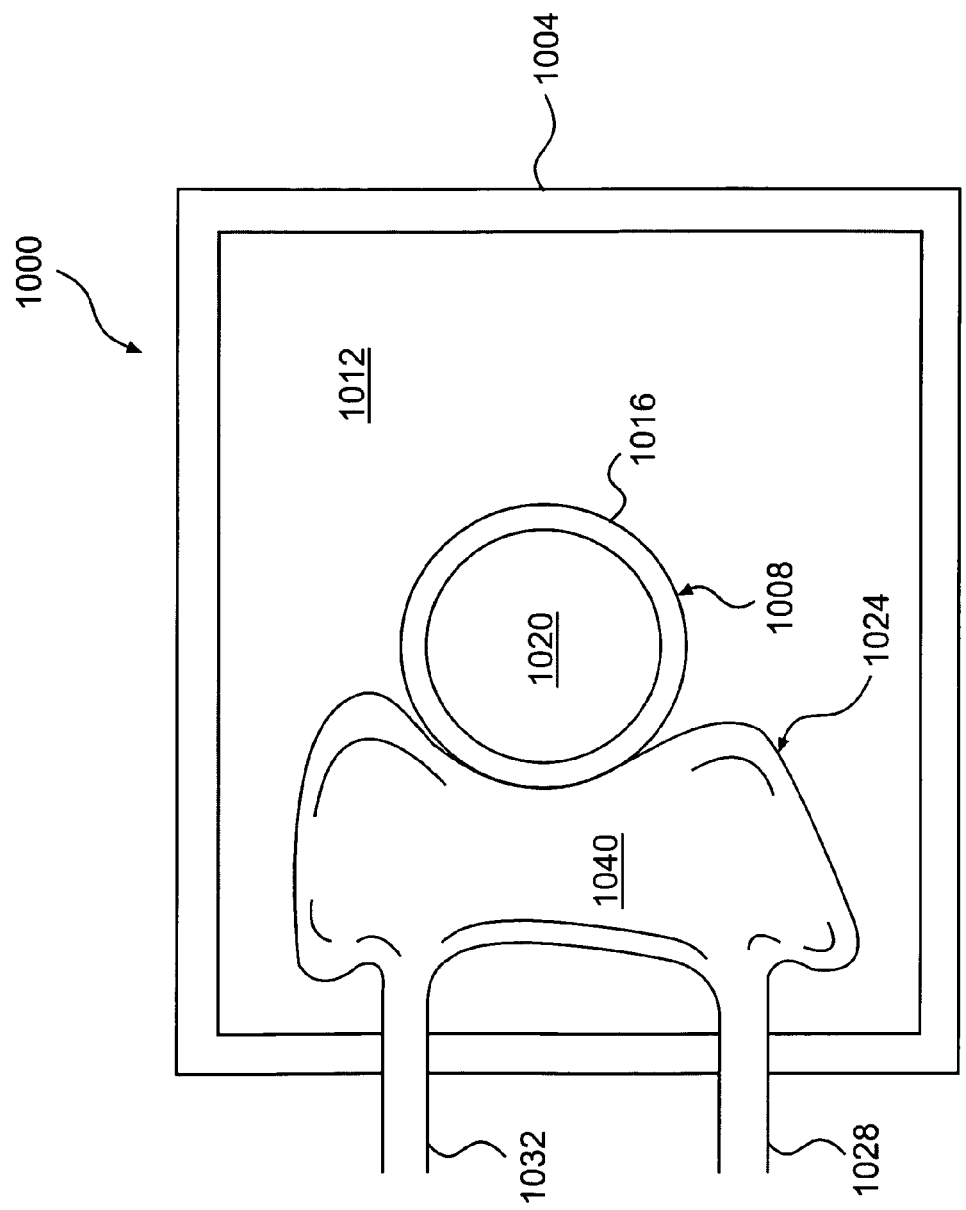

Referring now to FIGS. 1B and 1C, the temperature-control bladder 1024 has minimal or no contact to the reaction chamber 1008 in a disengaged position (FIG. 1B). The introduction of the temperature-control fluid into the temperature-control bladder 1024 induces expansion of the temperature-control bladder 1024 and converts the temperature-control bladder 1024 from the substantially non-abutting disengaged position (FIG. 1B) to an engaged position in which the temperature-control bladder 1024 abuts at least a portion of the chamber wall 1016 (FIG. 1C). The direct contact between the temperature-control bladder 1024 and the chamber wall 1016 allows for thermal exchange between the temperature-control fluid and the internal volume 1020 of the reaction chamber 1008. In one embodiment, the temperature-control bladder 1024 contains a surface of high thermal conductivity and is so configured that the surface of high thermal conductivity abuts the chamber wall 1016 when the temperature-control bladder 1024 is filled with the temperature-control fluid.

Therefore, the temperature of the internal volume 1020 of the reaction chamber 1008 can be can be modulated in a controlled fashion by introducing the temperature-control fluid into the temperature-control bladder 1024 to establish thermal contact between the temperature-control bladder 1024 and the reaction chamber 1008, and withdrawing the temperature-control fluid from the temperature-control bladder 1024 to disengage the temperature-control bladder 1024 from the reaction chamber 1008. Alternatively, the temperature of the internal volume 1020 of the reaction chamber 1008 can be modulated by replacing the temperature-control fluid in the interior 1040 of the temperature-control bladder 1024 with temperature-control fluid of a different temperature without disengaging the temperature-control bladder 1024 from the reaction chamber 1008.

Examples of the temperature-control fluid include, but are not limited to, water, salt water, antifreeze, oil, and silicone. Other suitable temperature-control fluids, means for regulating the temperature of such fluids, and means for introducing such fluids to, and withdrawing them from, the bladder are also familiar to those having ordinary skill in the art. In one embodiment, the temperature-control fluid is a gel material, the means for introducing the temperature-control fluid into and withdrawing the temperature-control material from the bladder is a pump, and the means for regulating the temperature of the temperature-control fluid is a resistive or peltier heater.

Figure 2:
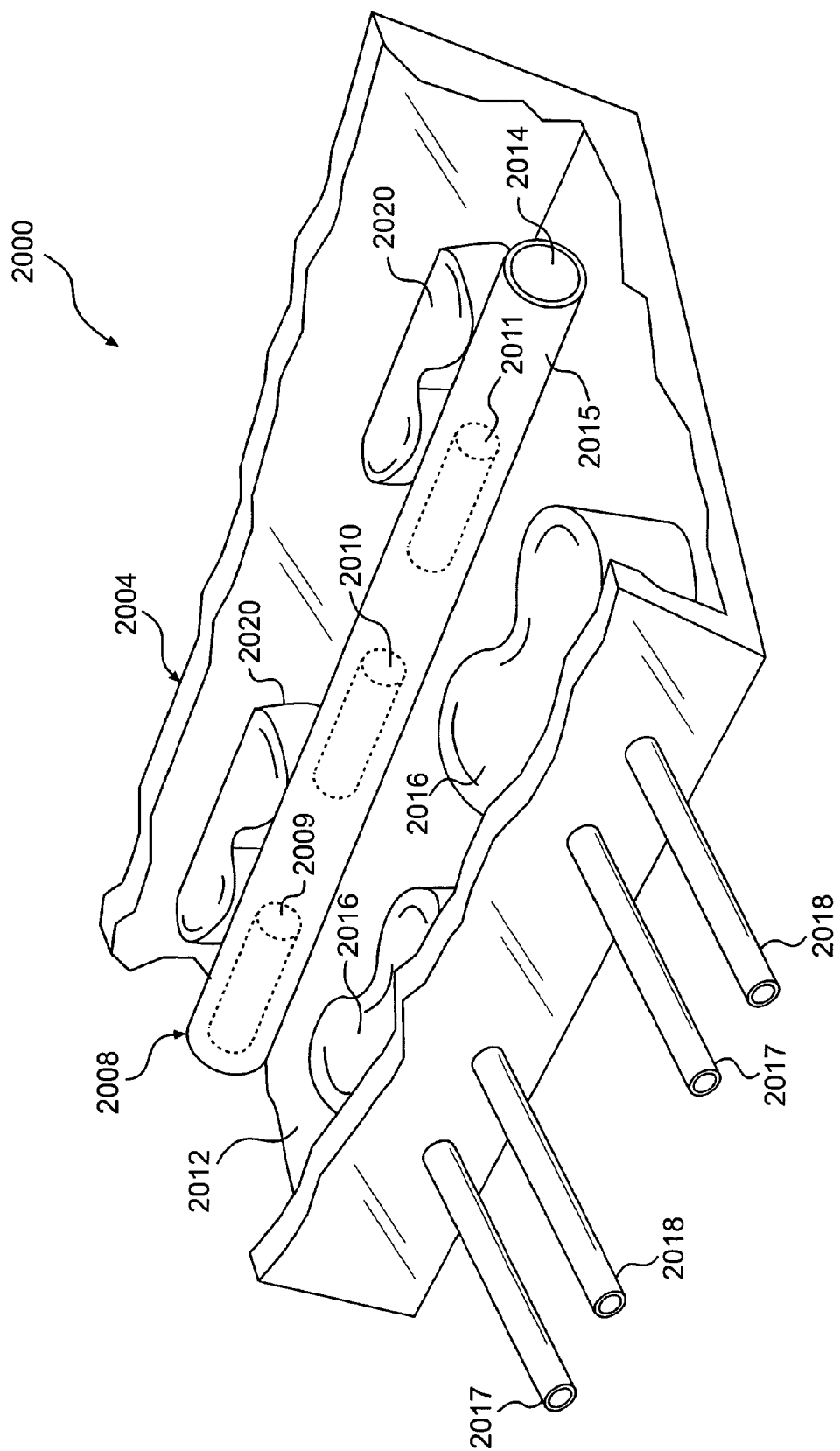
FIG. 2 is a partial cut-away view of another embodiment of a device in accordance with the present invention that comprises multiple sets of bladders.

FIG. 2 shows another embodiment of a housing 2004. In this embodiment, the reaction chamber 2008 has a substantially tubular design through which reaction mixtures 2009, 2010 and 2011 travel in defined and disjoint volumes, commonly referred to as "slugs," through the interior space 2014 of the reaction chamber 2008. Proximally adjacent the reaction chamber 2008 are two sets of temperature-control bladders (2016 and 2020) arrayed in pairs on opposing sides of the reaction chamber 2008. Each of the bladders 2016 and 2020 is connected to a reservoir of temperature-control fluid via inlet 2017 and outlet 2018. The bladders 2016 and 2020 operate as described above, i.e., engaging with the reaction chamber 2008 after being filled with a temperature control-fluid. In one embodiment, the slugs are transported through the internal volume 2014 of the reaction chamber 2008 and paused at defined locations whereupon one or more the bladder pairs engages the outer wall 2015 of the reaction chamber 2008 to modulate the temperature of the slug by thermal exchange as described above. In one embodiment, the bladders 2016 and 2020 are filled with a temperature-control fluid at a single temperature to provide substantially equal heat exchange by all bladders. In another embodiment, different bladders hold temperature-control fluid at different temperatures. In another embodiment, different bladders hold different temperature-control fluids to provide different thermal exchange properties.

In another embodiment, the housing includes one or more temperature-control bladders but does not include a reaction chamber of a fixed shape or volume. An opening on the housing allows the insertion of a reaction chamber, such as a PCR tube or a microarray slide, in the vicinity of the temperature-control bladder. The temperature-control bladder, when inflated with a temperature-control fluid, expands inside the housing and forms a direct contact to the exterior of the inserted reaction chamber. This design allows the flexible surface of the temperature-control bladder to conform to the contour of the exterior surface of the reaction chamber, thus providing efficient heat transfer between the temperature-control bladder and the reaction chamber.

Figure 3:
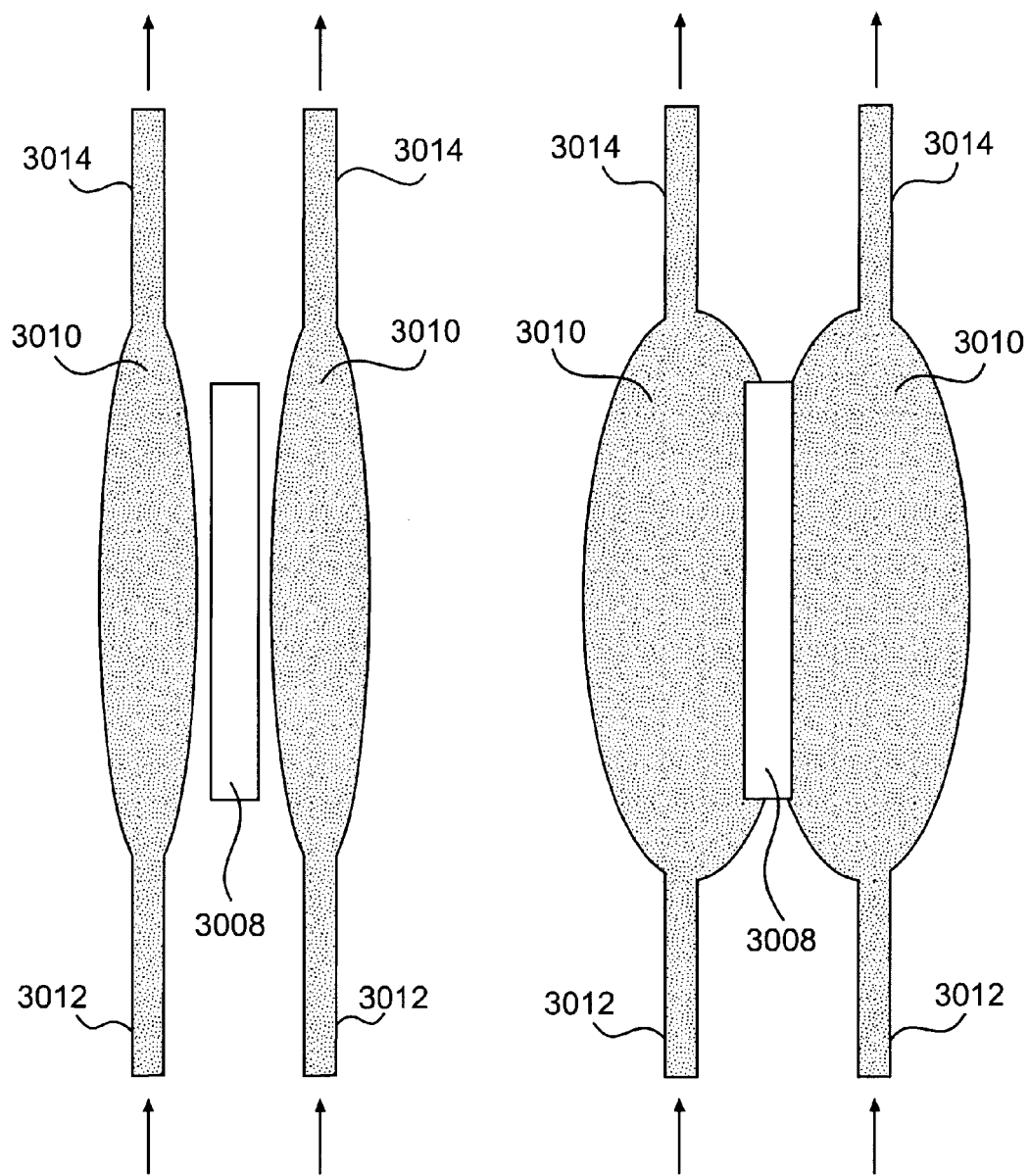
FIG. 3 is a schematic illustrating an elongated design of a bladder assembly.

A person of ordinary skill in the art would understand that the shape of the temperature-control bladder can vary considerably, ranging from spherical to an elongated tubular design. FIG. 3 shows a heating arrangement for a microarray slide (3008) using a pair of temperature-control bladders 3010. In this embodiment, the temperature-control bladders 3010 have an elongated tubular shape to accommodate rectangular reaction chamber geometries. Multiple microarray slides or reaction tubes may be positioned between the bladder pair 3010. An inlet 3012 and an outlet 3014 are positioned at opposing ends of the temperature-control bladder 3010. The inlets 3012 and outlets 3014 are connected to a heated fluidic plumbing or circuitry for thermal cycling. In one embodiment, the temperature-control bladders 3010 are pouches created using two sheets of flexible material that are cut to shape and bonded or welded to each other along the perimeter.

Figure 4B:
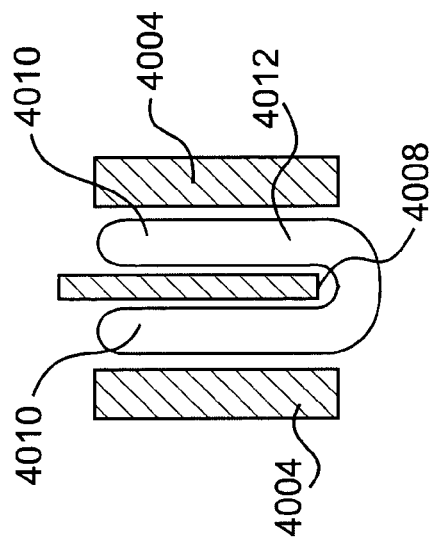
FIGS. 4A and 4B are schematics illustrating a folding design of a bladder assembly.
Figure 4A:
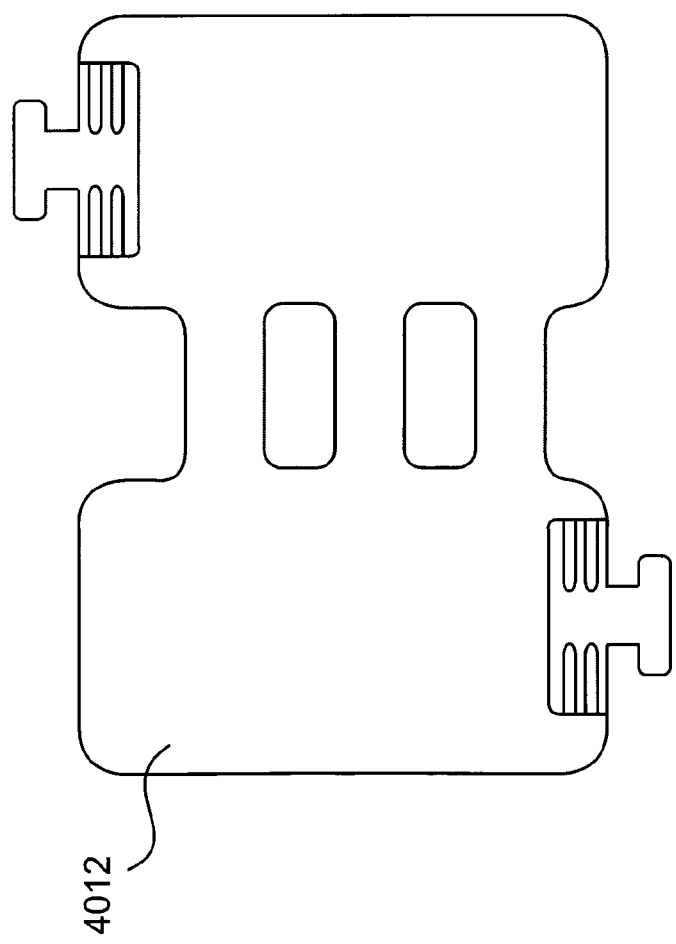

In another embodiment, a single temperature-control bladder 4012 (FIG. 4A) is folded into a U-shape inside a housing 4004 to form a pair of temperature-control bladder arms 4010 (FIG. 4B) that abut the reaction chamber 4008, when the temperature-control bladder 4012 is filled with a temperature-control fluid.

In yet another embodiment, one or more temperature-control bladders 4012 are configured to receive the reaction chamber 4008 without the housing 4004.

Figure 5A:
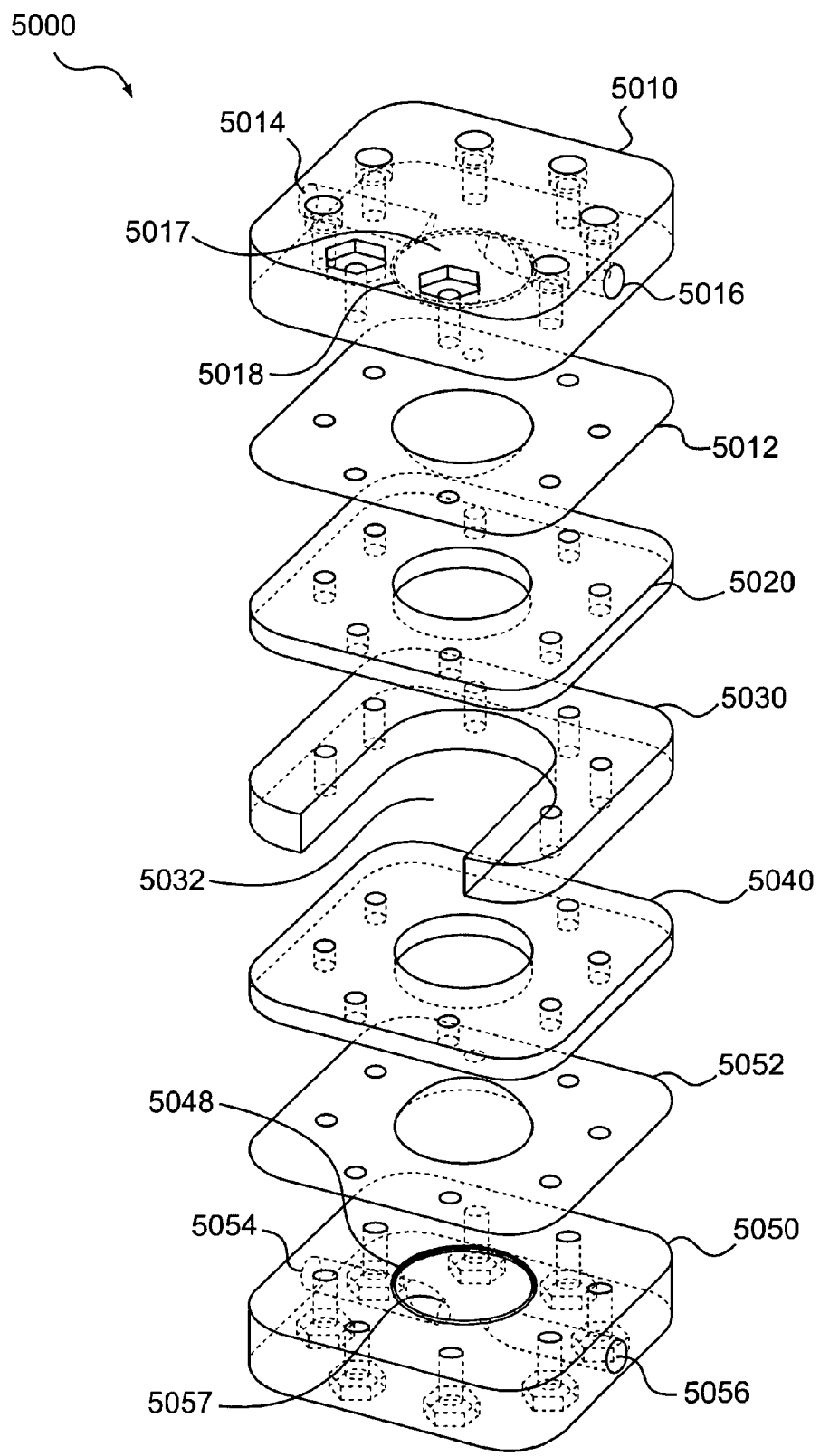

FIGS. 5A-5D show another configuration of a temperature-control bladder assembly. In this embodiment, the housing that holds the bladders and reaction chamber is formed by a modular assembly 5000. As shown in FIG. 5A, the modular assembly 5000 includes an upper bracket 5010 enclosing a temperature-control bladder 5012, a first cushion 5020, a middle bracket 5030, a second cushion 5040, and a lower bracket 5050 enclosing a temperature-control bladder 5052. The temperature-control bladders 5012 and 5052 are made with a flexible and heat conductive material and interface with a circulating temperature-control fluid via inlet ports (5014, 5054) and outlet ports (5016, 5056) on the upper and lower brackets 5010 and 5050. The inlet ports and outlet ports are positioned at the bracket at the base of the temperature-control bladder to connect with the fluidics and allow the temperature-control fluid to enter and exit the temperature-control bladders 5012 and 5052. The base of the temperature-control bladder 5012 or 5052 is sealed at bracket 5010 or 5050 with o-ring 5018 or 5048, respectively. The middle bracket 5030 is a U-shaped bracket which, when assembled with the other modules of the modular assembly 5000, defines an interior space 5032 that is accessible through an opening 5034. For a particular application, the opening 5034 and the interior space 5032 are designed to have a size an shape to receive a reaction chamber used in that application.

Each of the bracket 5010 and 5050 contains an opening 5017 or 5057 that opens to the interior space 5032. During operation, the temperature-control fluid fills and pressurizes the temperature-control bladders 5012 and 5052, which expand through the openings 5017 and 5057 and form a pair of pillow shaped temperature-control surfaces that squeeze firmly against the upper and lower sides of the reaction chamber.

Figure 5D:
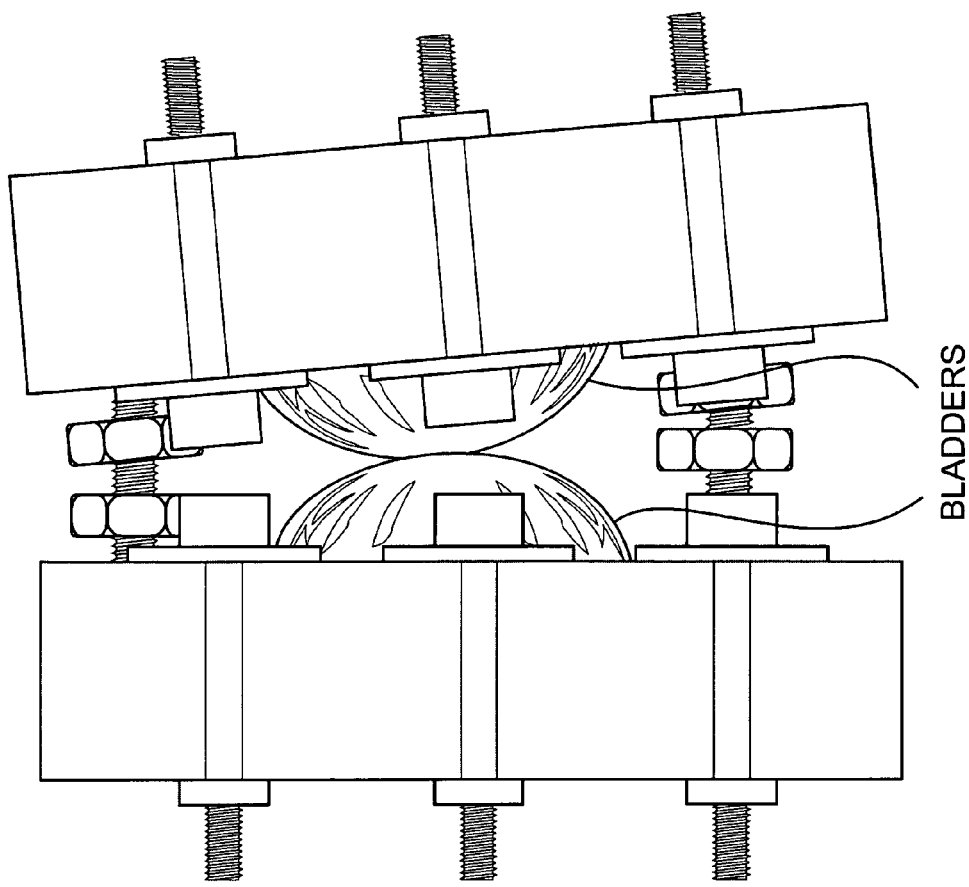
Figure 5C:
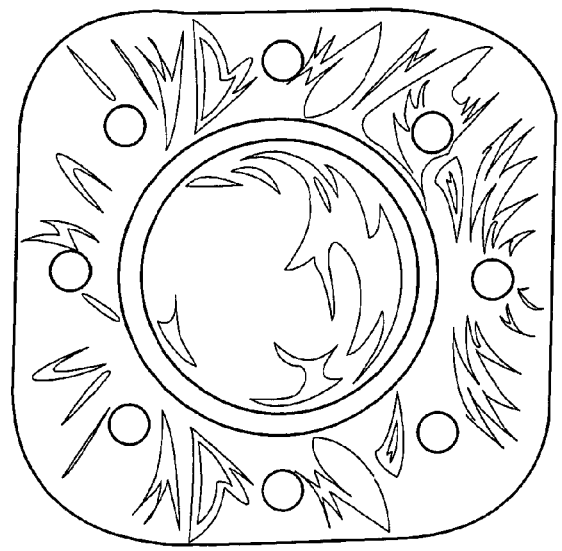

FIG. 5B shows an assembled modular assembly 5000 with the opening 5034 to receive the reaction chamber. FIG. 5C is a close-up drawing of a pillow-shaped bladder which can be inflated with a temperature control fluid after being sealed between a bracket and a cushion. FIG. 5D shows a bladder assembly with a pair of inflated bladders. A reaction chamber in the form of a slide, a tube, or a cartridge may be held between the two inflated bladders.

In another embodiment, the substance (which may be in the form of one or more slugs) contained in the internal volume of the reaction chamber is a mixture of reagents for performing a PCR reaction. In a more specific embodiment, the reaction chamber is a disposable analytical cartridge, such as available commercially, that holds the PCR reagents. One particular embodiment includes a single, static reaction chamber containing reactants for a PCR amplification of an oligomer. One or more temperature-control bladder(s) is (are) brought into contact with the reaction chamber, each of which bladders contain the same circulating temperature-control substance.

In another embodiment, a valve diverts the temperature-control fluid from two or more reservoirs of temperature-control fluid that are at different temperatures, so that the PCR mixture in the reaction chamber can be brought to different temperatures by exchanging the temperature-control fluids in the temperature control bladders. During the thermal cycling, for example, a temperature-control fluid at 95° C. is circulated into the temperature-control bladders to heat, and thereby denature the oligomers, and then withdrawn. Next, a temperature-control fluid at 60° C. is circulated into the temperature bladders to enable the primers to hybridize and extend to generate PCR amplication product. This sequence is performed for between about 30 and about 50 cycles.

In another embodiment, two temperature-control bladders are brought into contact with a single reaction chamber, wherein each bladder contains a circulating temperature-control substance at a different temperature (e.g., one at 95° C. and the other at 60° C.). Expansion and contraction of the temperature bladders as described above determines which bladder makes contact with the reaction chamber or channel.

In still another embodiment, a single reaction chamber has two or more reaction zones in a single channel. Each zone interfaces with a different temperature control bladder; and each bladder is at a different temperature e.g., 95° C. and 60° C. respectively. The reaction slug is moved hack and forth between temperature zones to produce the desired thermal cycling. (See FIG. 2, described above.)

In other embodiments, one or more of the temperature-control bladders is replaced by a resistive heater, a peltier, or temperature-controlled air, either singly or in combination.

In still other embodiments, the above-described reaction chamber is replaced with a microarray having immobilized primers at each microarray spot.

In still other embodiments, the bladder thermal cycler comprises at least one temperature-control bladder configured to receive a reaction chamber; and at least one fluid control device that delivers a temperature-control fluid to the temperature-control bladder at a desired temperature. Each temperature-control bladder comprises a flexible, heat conductive surface that comes in contact with the reaction chamber when the temperature-control bladder is inflated with the temperature-control fluid.

Figure 6:
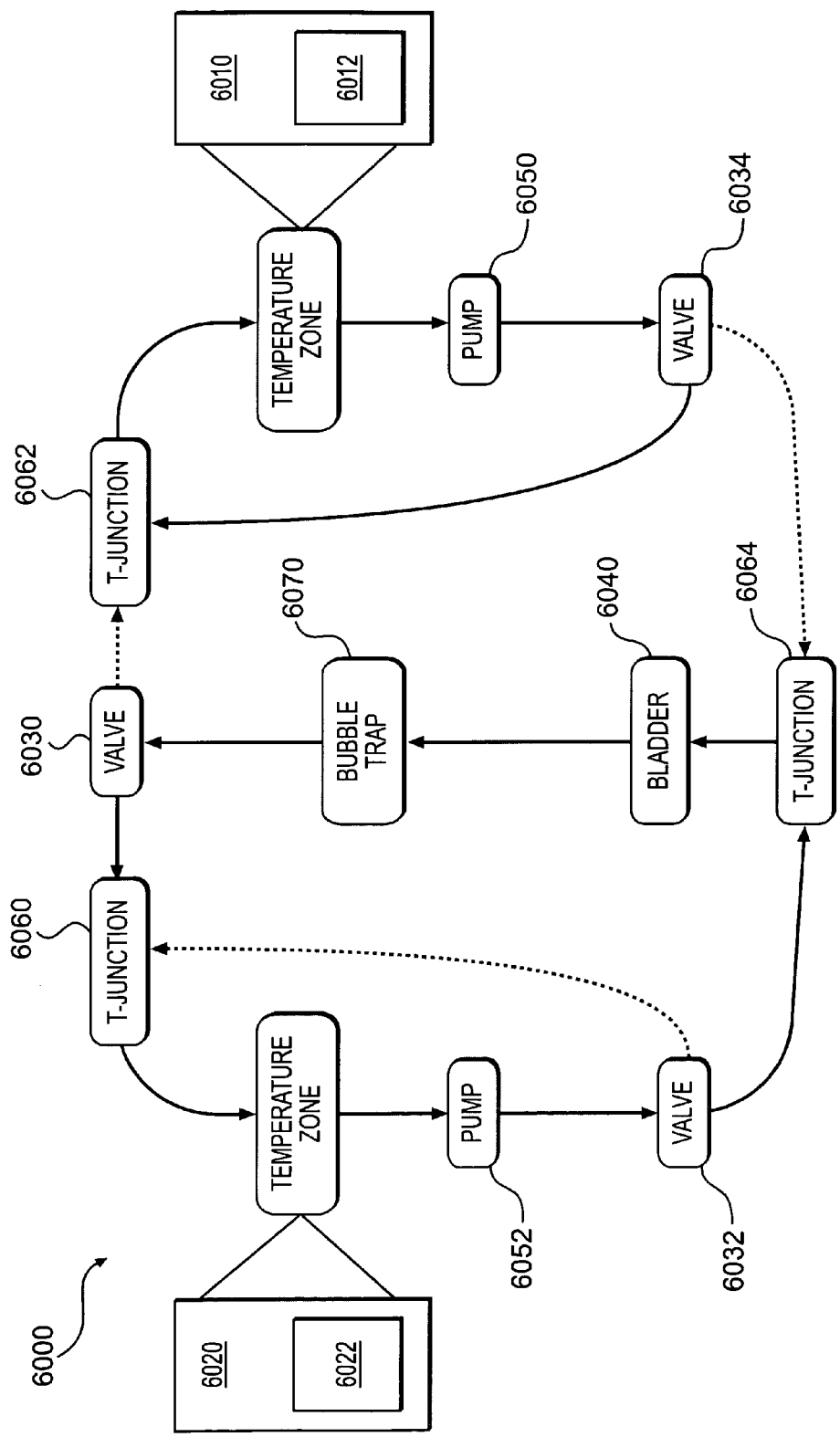
FIG. 6 is a schematic showing an embodiment of a bladder thermal cycler with a dual-loop circulation.

In one embodiment, a bladder thermal cycler is constructed with a temperature-control fluid cycling through a bladder assembly alternatively at two or more temperatures. FIG. 6 is a fluid flow diagram showing a bladder thermal cycler 6000 with two temperature zones 6010 and 6020, and a dual-loop circulation system. This device utilizes a first temperature zone heat exchanger 6012 and a second temperature zone heat exchanger 6022 as the source of temperature control. The heat exchangers 6012 and 6022 each contains one or more heater or heater/cooler devices that maintains a steady-state temperature in each temperature zone at the user's specified set point. Coordinated valves 6030, 6032 and 6034 direct the temperature control fluid from either the temperature zone 6010 (kept at a temperature of, for example, 80-105° C.) or the temperature zone 6020 (kept at a temperature of, for example, 50-70° C.) to flow through the bladder 6040 while the pumps 6050 and 6052 continue in one direction and re-circulate the fluid in the respective zones through T-junctions 6060, 6062 and 6064. The temperature-control bladder 6040 is positioned immediately downstream of the temperature zones in order to minimize heat loss. In one embodiment, the device 6000 further comprises a bubble trap 6070 that removes bubbles from the temperature control fluid. The pumps 6050 and 6052 may have fixed or variable speed. Variable speed offers the benefit of better fluid pressure control for bladder expansion and contraction. It also allows fine tuning of temperature control, for example, by utilizing a feedback loop between the temperature sensors and the pump speed control.

In one embodiment, the valves, pumps, and heat exchangers in the device 6000 are controlled by a system controller using software that contains a thermal cycling protocol. The system controller provides coordination and communication of the components in the bladder thermal cycler 6000. The system controller is designed to: (a) provide a single user interface to the entire system; (b) allow a user to quickly determine the status of all components associated with the system; and (c) accept input to change parameters which allow for the configuration changes. In one embodiment, the system controller includes a memory, a controller, and an external port. The memory may be used to store thermal cycling protocols. In one embodiment, the memory is a flash memory. The controller monitors and controls the operation of the bladder thermal cycler 6000 and provides an interface to the user about the status of the overall system. For example, the controller may stage the cycling timing and temperature of the temperature-control fluid in the bladder thermal cycler 6000.

In one embodiment, the controller is small, lightweight and available as a standard commercial off-the-shelf (COTS) product. In another embodiment, the controller is a COTS offering and is packaged as a microbox PC with a passive PCI bus backplane. This configuration allows the component modularity for easy upgrades as computer hardware technologies improve. In another embodiment, the controller resides on a single board computer (SBC) that already have its peripheral interfaces built in: PCI bus, Ethernet, and RS-232 serial. Flash memory and DRAM can be sized to the control system requirements with removable memory sockets on the SBC. Communication from the controller to the other components of the bladder thermal cycler 6000 is handled by COTS data acquisition, digital input/output, and analog input/output circuit cards that are PCI bus compatible.

The external port is used for downloading software upgrades to the memory and performing external troubleshooting/diagnostics. In one embodiment, the bladder thermal cycler 6000 is powered by a long-life battery or batteries that can be recharged and reused.

In one embodiment, the steady-state temperature in each temperature zone 6010 or 6020 is maintained by a proportional-integral-derivative controller (PID controller). PID control is a generic control loop feedback mechanism widely used in industrial control systems and is well-known to one skilled in the art. In another embodiment, the PID control is replaced with other types of control such as fuzzy control. A fuzzy control system is a control system based on fuzzy logic - a mathematical system that analyzes analog input values in terms of logical variables that take on continuous values between 0 and 1, in contrast to classical or digital logic, which operates on discrete values of either 0 and 1 (true and false). Fuzzy control systems are also well-known to one skilled in the art.

Unlike some prior art devices, such as the liquid-based thermal cycler by Lawrence Berkeley National Lab, which use large reservoirs or drums of heated fluid to drive the thermal cycling, the bladder thermal cycler 6000 is capable of operation without reservoirs of heated fluid. In one embodiment, the temperature-control fluid is heated in custom-built, in-line heaters in the heat exchanger 6012 or 6022 as the temperature-control fluid passes through the temperature zone 6010 or 6020, respectively. The heated temperature-control fluid is re-circulated to reduce the volume of the fluid required to heat the temperature-control bladder(s) 6040. The smaller fluid volume in turn allows the use of substantially smaller heater/cooler devices in the heat exchanger 6012 or 6022.

Figure 7:
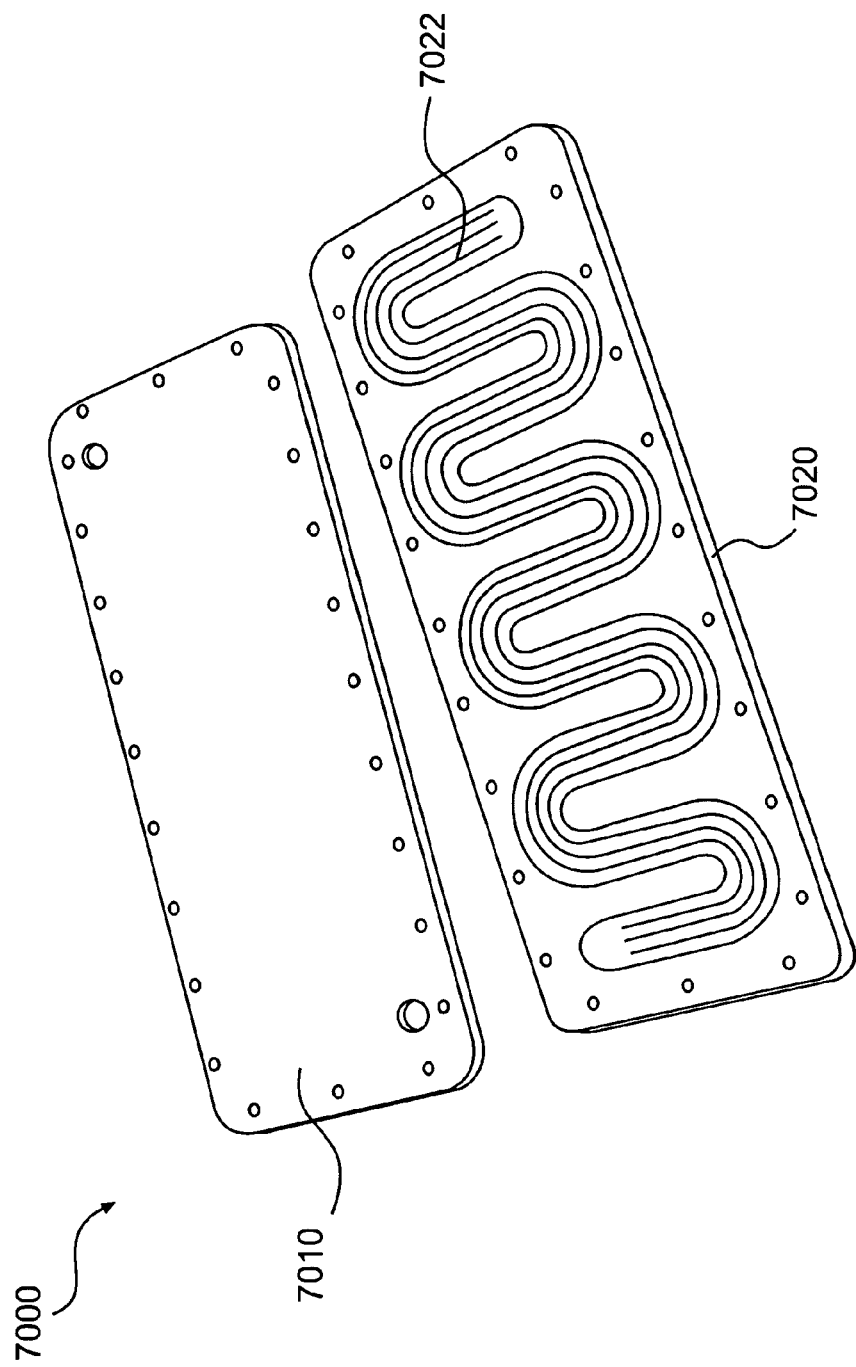
FIG. 7 is a diagram showing an aluminum block for heat exchangers.

In one embodiment, the heater devices each consists of two heating blocks with one or more cartridge heaters embedded in each heating block, and a thermocouple. Referring now to FIG. 7, in one embodiment, the heating block 7000 includes a cover 7010 and a base 7020. The base 7020 contains parallel serpentine channels or fins 7022 for rapid, efficient heating of the circulating temperature-control fluid as it flows through the heating block 7000. The thermocouple (not shown) in the heating block 7000 monitors the temperature in the heating block 7000 and allows PID control of the block temperature. The heating block 7000 is typically made of a heat conductive material, such as a metal or an alloy. In one embodiment, the heating block 7000 is made of aluminum.

EXAMPLES

Example 1

Bladder Thermal Cycler With Single-loop Circulation

Figure 8:
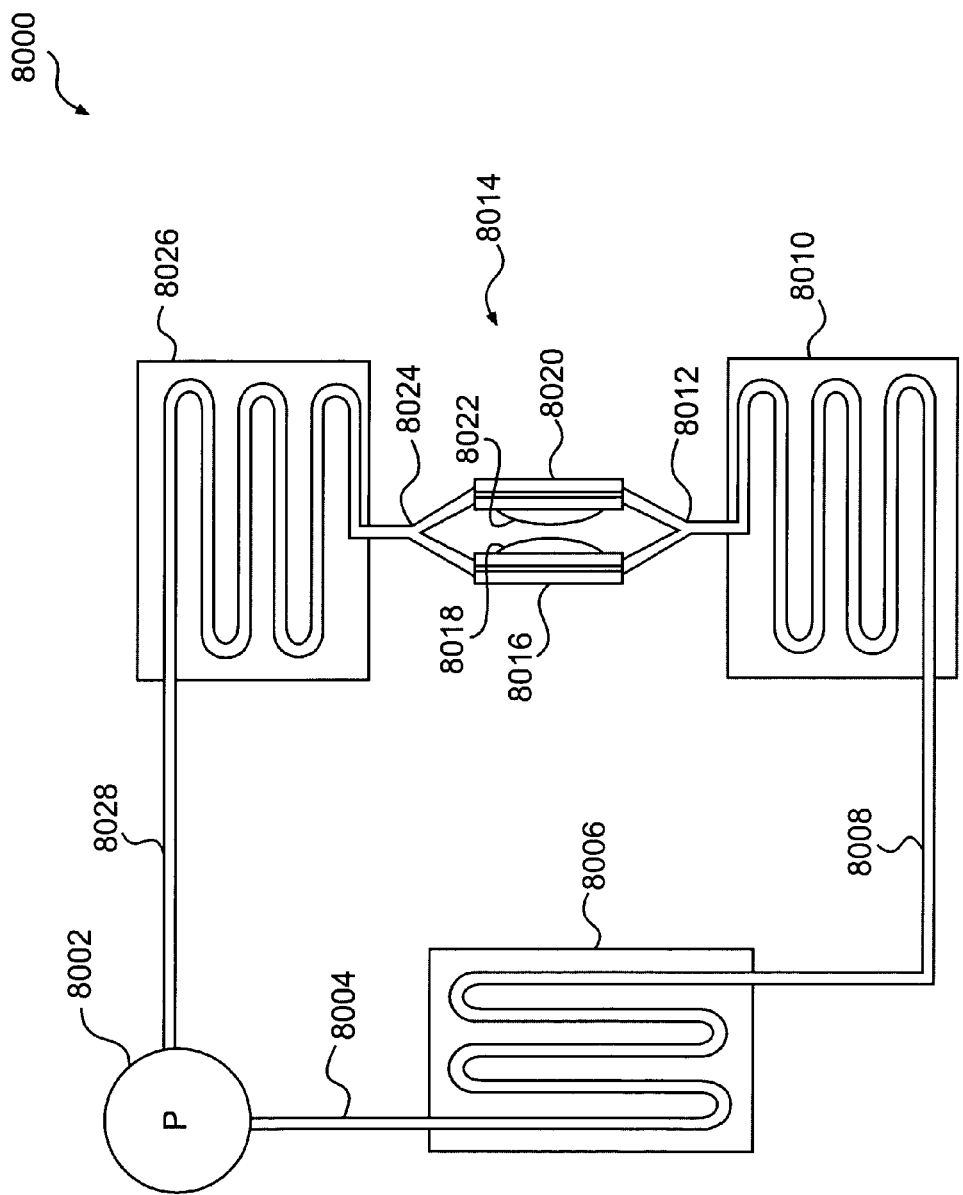
FIG. 8 is a schematic showing an embodiment of a bladder thermal cycler with a single-loop circulation.

FIG. 8 provides a schematic illustration of one embodiment of a single-loop circulation bladder thermal cycler 8000. A pump 8002 of standard construction as will be understood by those having ordinary skill in the art, is connected to an outlet line 8004 that carries water through a heat exchanger 8006 made using materials known to persons having ordinary skill in the art. The outlet line from the heat exchanger 8008 carries the water to a first heater 8010 configured to heat the water to about 95° C. The water then passes through a branch 8012 that splits the path into the bladder unit 8014, which includes a first bladder support 8016 coupled to a first bladder 8018 in a substantially opposing arrangement to a second bladder support 8020 coupled to a second bladder 8022. Water exiting the bladder unit 8014 is combined back into a single path by a second branch 8024 and then passes into a second heater 8026 configured to heat the water to about 65° C. A return path 8028 brings the water back to the pump. Each of the bladders has a capacity of five milliliters (ml), each of the heaters can hold 22 ml, and the heat exchanger can hold between 5 ml and 22 ml. By cycling the water reversibly between each of the heaters and heat exchanger, the bladders can cycle the temperature of a sample held in the bladder unit between a nominal starting temperature, 65° C., and 95° C.

Figure 9:
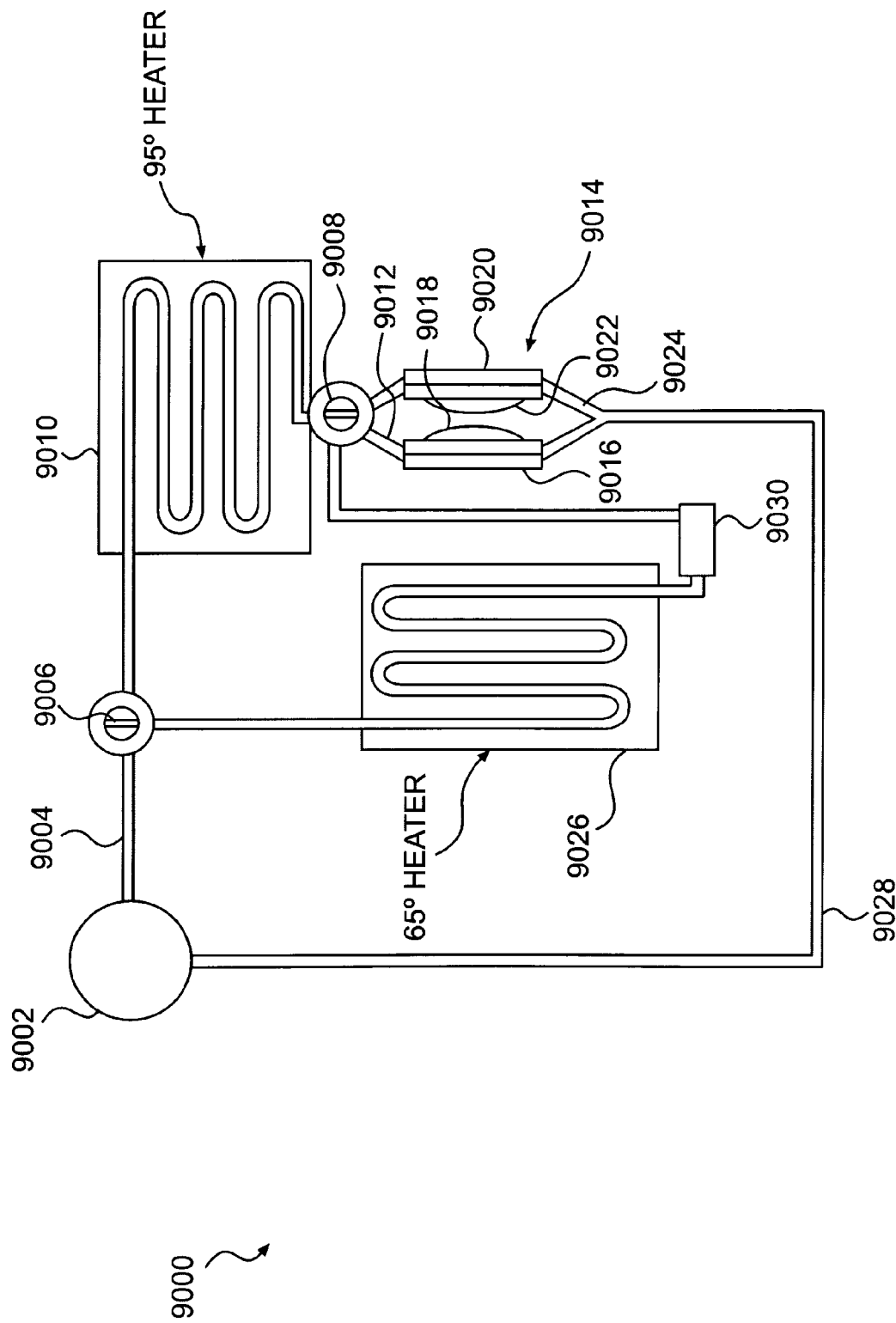
FIG. 9 is a schematic showing a second embodiment of a bladder thermal cycler with a single-loop circulation.

FIG. 9 provides a schematic illustration of another embodiment of a single-loop circulation bladder thermal cycler 9000. A pump 9002 of standard construction as will be understood by those having ordinary skill in the art, is connected to an outlet line 9004 that carries water through a two-way valve 9006 to a first heater 9010 configured to heat the water to about 95° C. The water then passes through a second two-way valve 9008 and a branch 9012 that splits the path into the bladder unit 9014, which includes a first bladder support 9016 coupled to a first bladder 9018 in a substantially opposing arrangement to a second bladder support 9020 coupled to a second bladder 9022. Water exiting the bladder unit 9014 is combined back into a single path by a second branch 9024. A return path 9028 brings the water back to the pump. Water is moved back to the two-way valve 9006 and diverted into a second heater 9026 configured to heat the water to about 65° C. The water then passes through a bubble trap 9030 and a second two-way valve 9008 to enter the bladder unit 9014 through the branch 9012. In one embodiment, each of the bladders 9018 and 9022 has a capacity of five milliliters (ml)

and each of the heaters can hold 22 ml. By cycling the water between each of the heaters, the bladders can cycle the temperature of a sample held in the bladder unit between a nominal starting temperature, 65° C., and 95° C.

Figure 10:
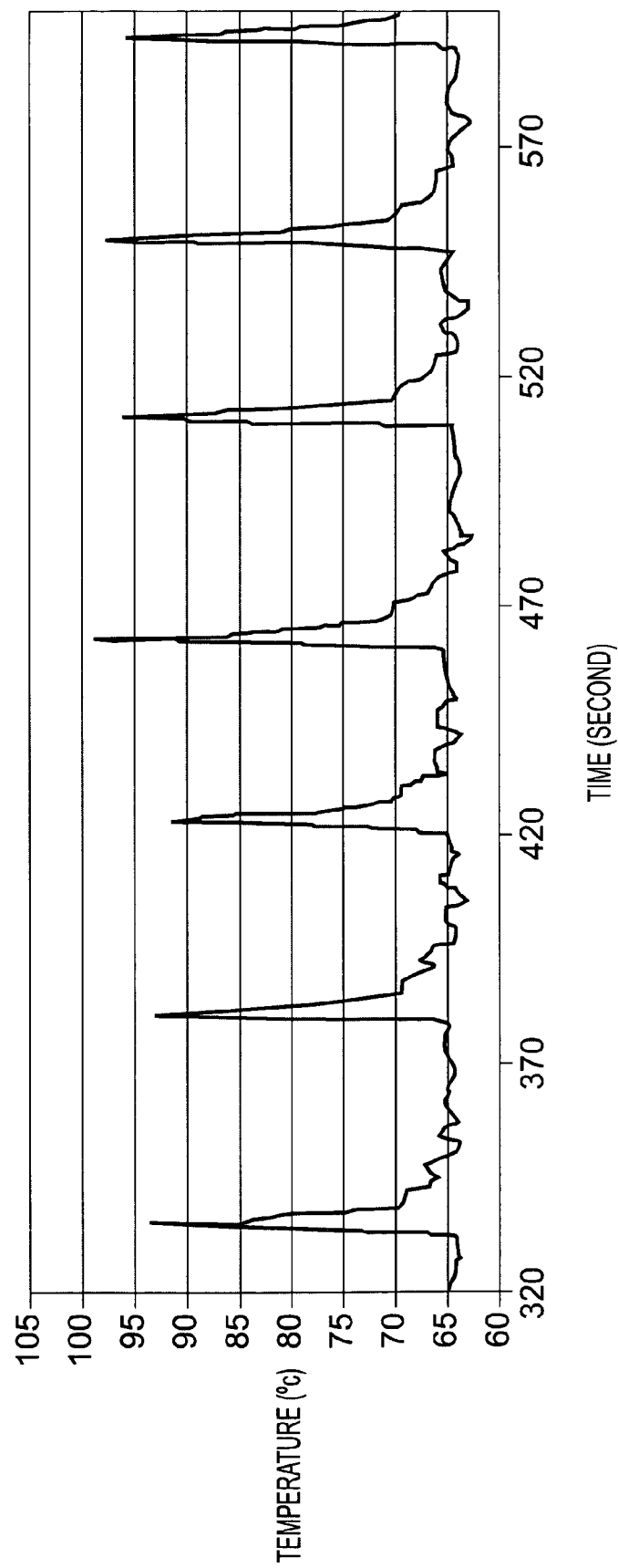
FIG. 10 is a graph showing heating and cooling as a function of time for the embodiment illustrated in FIG. 9.

FIG. 10 shows a thermal cycling experiment using the device described with reference to FIG. 9. In this experiment, water in a reaction chamber was cooled from 95° C. to 65° C., held at 65° C. for about 25 seconds, heated to about 95° C., held at that temperature for about one second, and then cooled again to about 65° C. The temperature curve showed rapid heating and cooling rate (about 15° C./sec for heating and 6° C./sec for cooling), Example 2

Bladder Thermal Cycler With Dual-loop Circulation

Figure 11:
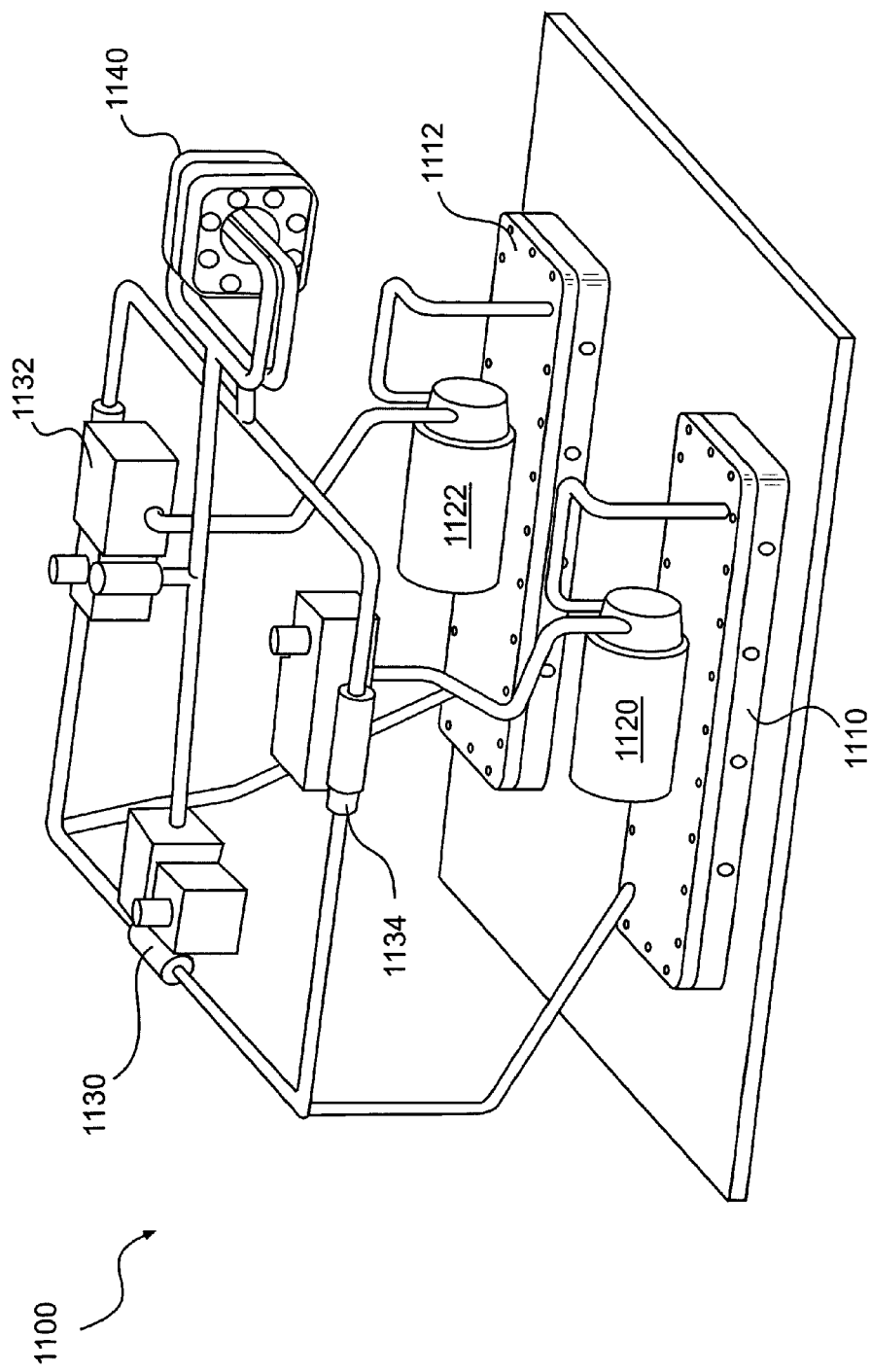
FIG. 11 is a schematic showing the major components of a dual-loop circulation bladder thermal cycler.

A prototype bladder thermal cycler is constructed based on the dual-loop circulation design shown in FIG. 6. FIG. 11 is a diagram showing the major components of the bladder thermal cycler. The dual-circulation bladder thermal cycler 1100 includes heat exchange blocks 1110 and 1112, pumps 1120 and 1122, two-way valves 1130, 1132 and 1134, and a temperature-control bladder assembly 1140 with the modular design shown in FIG. 5. A reaction chamber (not shown) is placed in an interior space flanked by two temperature-control bladders in the temperature-control bladder assembly 1140. Temperature-control fluid of a first temperature circulates through the temperature-control bladder assembly 1140 via a first circulating loop that includes heat exchange block 1110, pump 1120, two-way valves 1134 and 1130. Temperature-control fluid of a second temperature circulates through the temperature-control bladder assembly 1140 via a second circulating loop that includes heat exchange block 1112, pump 1122, two-way valves 1132 and 1130.

The actual prototype bladder thermal cycler has three levels. The bottom level of the instrument contains two heat exchangers and two pumps. The middle level contains three two-way valves and a modular bladder assembly that holds a reaction tube between a pair of temperature control bladders. The third level contains a power supply and four PID temperature controllers of which two control the two respective heat exchanger blocks, one controls the valves, and the fourth monitors the temperature in the reaction vessel or bladder. Approximately 100 ml of mineral oil was used as the circulating temperature-control fluid. There is no bona fide cooling device in the prototype bladder thermal cycler.

Example 3

Figure 12:
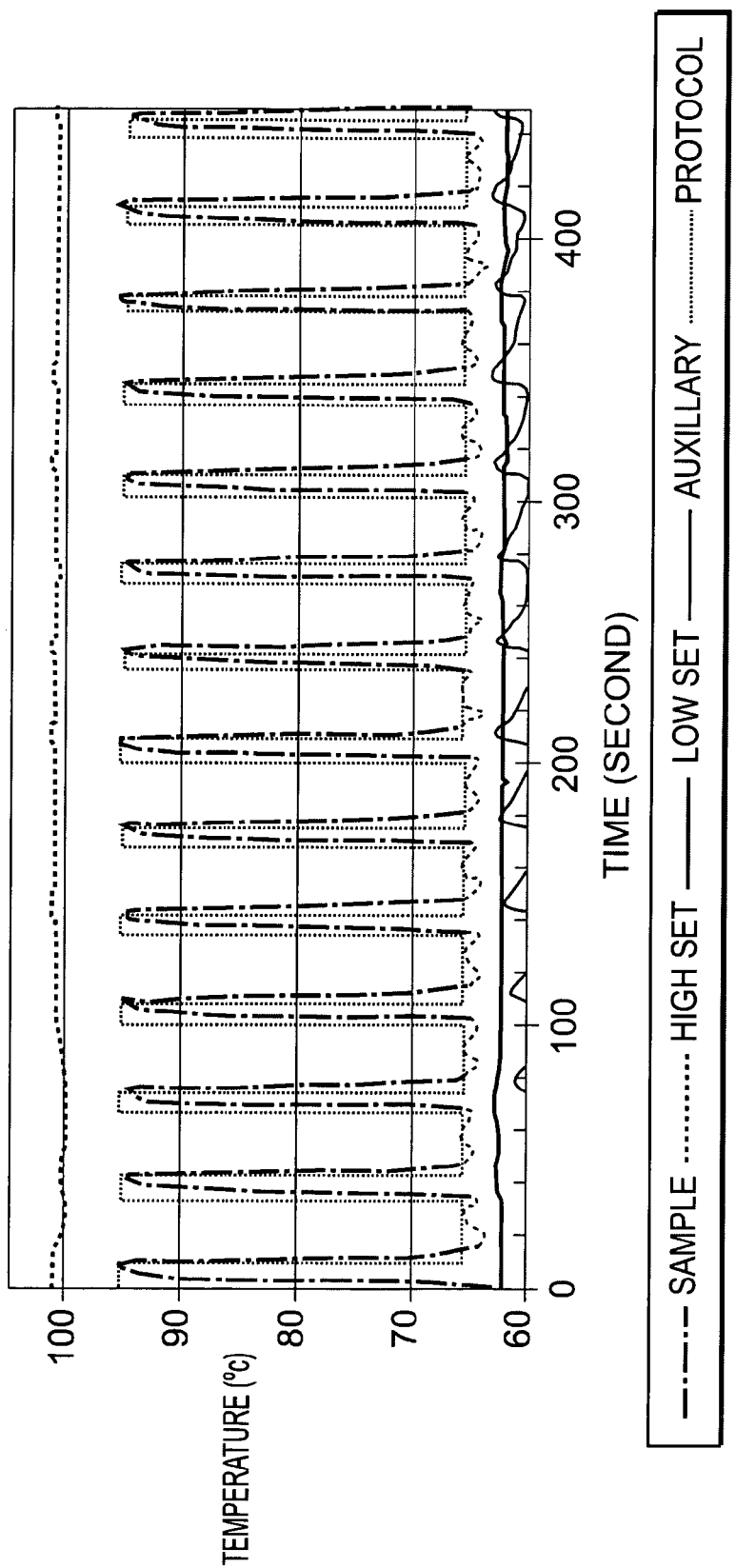
FIG. 12 is a diagram showing temperature measurements from a thermal cycling run of the dual-loop circulation bladder thermal cycler of FIG. 11.

Dual-loop Circulation Bladder Thermal Cycler Provides Satisfactory Thermal Cycling Profiles FIG. 12 shows temperature profiles of a thermal cycling run performed with the dual-loop circulation bladder thermal cycler described in Example 2. Temperatures inside the first heat exchange block 1110 (i.e., the hot zone), the second heat exchange block 1112 (i.e., the cold zone), and the reaction chamber were measured during the course of the run. As shown in FIG. 12, the hot zone and cold zone remain at steady-state. The zones are held at a slightly elevated temperature than the target temperature of the thermal cycling protocol to create a temperature offset that compensates for heat losses in the fluid paths from the temperature zones to the bladder assembly. This temperature offset can be minimized by reducing the path length that the circulating temperature control fluid has to travel and by utilizing insulation materials around the fluid paths. The successful thermal cycling temperature profile demonstrated that the principle of switching temperature control fluid through the bladder assembly can deliver the intended control of temperature in the reaction chamber.

Unlike conventional thermal cyclers, there is no need to program deliberate overshoots and undershoots of heater temperatures for the bladder thermal cycler due to the lag in the temperature change in the reaction chamber relative to that in the heat exchanger. The overshoots and undershoots are typically used to increase the heating and cooling ramp rate rates respectively. The controls for these overshoots and undershoots can be complex, requiring an algorithm that tightly controls the heater (e.g. resistive, piezoelectric) and cooling (thermoelectric, peizoelectric, refrigerant, fan, etc.) components.

The dual-loop circulation bladder thermal cycler is capable of performing rapid thermal cycling on microarray slides containing a reaction chamber. Conventional instruments such as the MJ Research griddle and tower (Global Medical Instrumentation, Inc., Ramsey, Minn.) typically require several hours to perform 40 cycles of PCR due to the slow ramp times. In addition, temperatures between array sites and within array sites can vary substantially. The dual-loop circulation bladder thermal cycler accomplishes thermal cycling of slides or flow cells containing a PCR reaction chamber in 40 min or less, while providing very uniform heat distribution and heat transfer. In addition, the bladder thermal cycler is capable of performing coupled thermal cycling and microarray hybridization.

Figure 13:
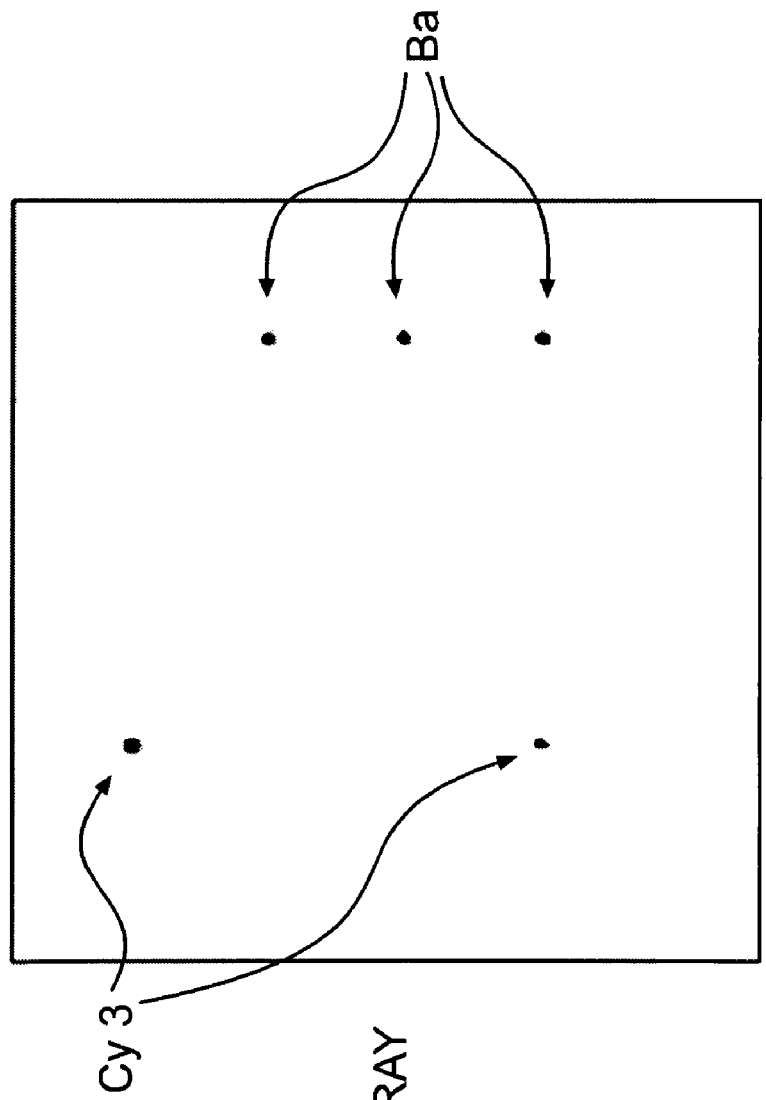
FIG. 13 is a picture showing fluorescence signals on a PCR/microarray slide after thermal cycling in the dual-loop circulation bladder thermal cycler of FIG. 11. Ba: probes for *Bacillus anthracis* DNA. Cy3: markers indicating orientation of the micro array.

Referring now to FIG. 13, a slide consisting of a microarray within a PCR reaction chamber was subjected to coupled PCR amplification and microarray hybridization of Bacillus anthracis genomic DNA. Ten copies of Bacillus anthracis genomic DNA were amplified using a fluorescently labeled primer. As shown in FIG. 13, positive fluorescence signal was detected at the probes complementary to the PCR product, indicating that the amplified Bacillus anthracis DNA product specifically hybridized to the respective complementary oligonucleotide probe immobilized on the surface within the chamber.

Although various specific embodiments and examples have been described herein, those having ordinary skill in the art will understand that many different implementations of the invention can be achieved without departing from the spirit or scope of this disclosure.

What is claimed:

1. A device for performing a polymerase chain reaction (PCR) in a reaction chamber, comprising:

a bladder assembly comprising:

a first temperature-control bladder configured to receive a temperature-control fluid from a first inlet channel and expel said temperature-control fluid from a first outlet channel, wherein said first temperature-control bladder comprises a flexible, heat conductive surface that comes in contact with at least a portion of an exterior surface of a reaction chamber after receiving said temperature-control fluid; and a second temperature-control bladder configured to receive said temperature-control fluid from a second inlet channel and expel said temperature-control fluid from a second outlet channel, wherein said second temperature-control bladder comprises a flexible, heat conductive surface that comes in contact with another portion of exterior surface of said reaction chamber after receiving said temperature-control fluid;

a first heat exchanger that is connected to both said first and second inlet channels via a first two-way valve and a first three-way connector, said first heat exchanger maintains said temperature-control fluid at a first temperature;

a second heat exchanger that is connected to both said first and second inlet channels via said first two-way valve and said first three-way connector, said second heat exchanger maintains said temperature-control fluid at a second temperature; and a pump located between said bladder assembly and said heat exchangers, said pump is connected to said first and second outlet channels via a three-way connector and is connected to either said first heat exchanger or said second heat exchanger via a second two-way valve.

2. The device of claim 1, wherein said reaction chamber is a tubular chamber.

3. The device of claim 1, wherein said reaction chamber is a slide chamber.

4. The device of claim 1, wherein said first heat exchanger comprises a heat conductive block comprising a cartridge heater and parallel serpentine channels or fins.

5. The device of claim 1, wherein said first heat exchanger comprises a thermocouple.

6. The device of claim 1, wherein said first heat exchanger maintains the temperature of the temperature-control fluid by PID control.

7. The device of claim 1, wherein said first heat exchanger maintains the temperature of the temperature-control fluid by fuzzy control.

8. The device of claim 1, further comprising a computer that controls said pump, said first and second heat exchangers, and said valves.

9. A bladder thermal cycler for performing PCR, comprising:
   a bladder assembly configured to receive a reaction chamber, said bladder assembly comprises:
      at least one temperature-control bladder having a thermal conductive surface, said temperature-control bladder is inflatable with a temperature-control fluid and said thermal conductive surface forms a contact with an exterior surface of a reaction chamber placed within said interior space when said temperature-control bladder is inflated, said bladder is configured to receive said temperature-control fluid from an inlet port and expel said temperature-control fluid from an outlet port;
   a first temperature control device capable of bringing said temperature-control fluid to a first temperature when said temperature-control fluid passes through said first temperature control device;
   a second temperature control device capable of bringing said temperature-control fluid to a second temperature when said temperature-control fluid passes through said second temperature control device;
   a first fluid control device that delivers said temperature-control fluid at said first temperature to said bladder assembly via a first two-way valve;
   a second fluid control device that delivers said temperature-control fluid at said second temperature to said bladder assembly via a second two-way valve; and
   a system controller that controls said temperature control devices and fluid control devices.

10. The bladder thermal cycler of claim 9, wherein said first and second temperature control devices each comprises a heating block comprising one or more fluid channels and a heater.

11. The bladder thermal cycler of claim 10, wherein said fluid channels are serpentine channels.

* * * * *